United States Patent
Eyolfson et al.

(10) Patent No.: US 6,369,887 B2
(45) Date of Patent: Apr. 9, 2002

(54) METHOD AND APPARATUS FOR AUTOMATED, IN SITU MATERIAL DETECTION USING FILTERED FLUORESCED, REFLECTED, OR ABSORBED LIGHT

(75) Inventors: Mark Eyolfson; Elton J. Hochhalter, both of Boise; Joe Lee Phillips, Nampa; David R. Johnson, Meridian; Peter S. Frank, Boise, all of ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 09/842,513

(22) Filed: Apr. 25, 2001

Related U.S. Application Data (60) Continuation of application No. 09/475,439, filed on Dec. 30, 1999, now Pat. No. 6,256,094, which is a division of application No. 08/964,451, filed on Nov. 4, 1997.

(51) Int. Cl.[7] .............................................. G01N 21/88
(52) U.S. Cl. ................... 356/237.4; 356/72; 250/458.1; 250/461.1
(58) Field of Search ................................ 356/317, 318, 356/417, 237.4; 250/458.1, 459.1, 461.1, 461.2

(56) References Cited

U.S. PATENT DOCUMENTS

| | | | |
|---|---|---|---|
| 4,312,732 A | 1/1982 | Degenkolb et al. | |
| 4,377,436 A | 3/1983 | Donnelly et al. | |
| 4,462,863 A | 7/1984 | Nishimatsu et al. | |
| 4,482,424 A | 11/1984 | Katzir et al. | |
| 4,586,822 A | 5/1986 | Tanimoto | |
| 4,609,428 A | 9/1986 | Fujimura | |
| 4,656,358 A | 4/1987 | Divens et al. | |
| 4,800,282 A | 1/1989 | Nishimura | |
| 4,816,686 A | 3/1989 | Hara et al. | |
| 4,846,920 A | 7/1989 | Keller et al. | |
| 5,162,867 A | 11/1992 | Kohno | |
| 5,176,790 A | 1/1993 | Arleo et al. | |
| 5,257,047 A | 10/1993 | Haneda et al. | |
| 5,264,328 A | 11/1993 | DellaGuardia et al. | |
| 5,312,717 A | 5/1994 | Sachdev et al. | |
| 5,350,236 A | 9/1994 | Thakur et al. | |
| 5,362,356 A | 11/1994 | Schoenborn | |
| 5,397,431 A | 3/1995 | Kadomura | |
| 5,434,026 A | 7/1995 | Takatsu et al. | |
| 5,444,265 A | 8/1995 | Hamilton | |
| 5,447,598 A | 9/1995 | Mihara et al. | |
| 5,483,568 A | 1/1996 | Yano et al. | |
| 5,489,362 A | 2/1996 | Steinhardt et al. | |
| 5,552,016 A | 9/1996 | Ghanayem | |
| 5,567,268 A | 10/1996 | Kadomura | |
| 5,654,237 A | 8/1997 | Suguro et al. | |
| 5,672,091 A | 9/1997 | Takahashi et al. | |
| 5,729,348 A | * 3/1998 | Romano | 356/417 |
| 5,780,857 A | * 7/1998 | Harju et al. | 250/458.1 |

FOREIGN PATENT DOCUMENTS

| | | |
|---|---|---|
| JP | 3-165518 | 7/1991 |
| JP | 8-220010 | 8/1996 |

* cited by examiner

Primary Examiner—F. L. Evans
(74) Attorney, Agent, or Firm—TraskBritt (57) ABSTRACT

A method and apparatus for detection of a particular material, such as photo-resist material, on a sample surface. A narrow beam of light is projected onto the sample surface and the fluoresced and/or reflected light intensity at a particular wavelength band is measured by a light detector. The light intensity is converted to a numerical value and transmitted electronically to a logic circuit which determines the proper disposition of the sample. The logic circuit controls a sample-handling robotic device which sequentially transfers samples to and from a stage for testing and subsequent disposition. The method is particularly useful for detecting photo-resist material on the surface of a semiconductor wafer.

17 Claims, 4 Drawing Sheets

METHOD AND APPARATUS FOR AUTOMATED, IN SITU MATERIAL DETECTION USING FILTERED FLUORESCED, REFLECTED, OR ABSORBED LIGHT

CROSS-REFERENCE TO RELATED APPLICATIONS

This application is a continuation of application Ser. No. 09/475,439, filed Dec. 30, 1999, now U.S. Pat. No. 6,256, 094B1, which is a divisional of and claims priority from application Ser. No. 08/964,451, filed Nov. 4, 1997, pending, the contents of which are incorporated by this reference.

BACKGROUND OF THE INVENTION

1. Field of the Invention

This invention relates generally to the manufacture of semiconductor wafers prepared by a method including applying a photo-resist layer, exposing the layer, and stripping the layer from the semiconductor wafer. More particularly, this invention pertains to a method for inspecting semiconductor wafers or other substrates to determine the presence of residual photo-resist material on the semiconductor wafer surface.

2. State of the Art

Semiconductor chips are produced in a multi-step process by which a plurality of identical electronic circuits is typically formed on a semiconductor substrate, such as a silicon wafer. The semiconductor substrate is then subdivided (diced) into individual chips which are further processed into semiconductor devices.

The electronic circuits are generally patterned into a semiconductor wafer by lithography. In this process, a resist material is coated onto the semiconductor wafer surface. As disclosed in commonly owned U.S. Pat. No. 5,350,236, issued Sep. 27, 1994, hereby incorporated herein by reference, the application of a material on a semiconductor substrate can be monitored by measuring light reflected from a surface of the semiconductor substrate.

After the resist material has been coated on the semiconductor wafer surface, it is selectively exposed to a radiation source, such as by the passage of radiation (i.e., light, e-beam, or X-rays) through a mask having the desired pattern. Some portions of the resist receive a high dosage of radiation while other portions receive little or no radiation, resulting in a difference in solubility from the resist portions. In a subsequent development step, a developer removes or etches portions of the resist coating from the semiconductor substrate at a rate higher than other portions. The selective removal results in a resist pattern which will become the electronic circuit pattern on the semiconductor substrate. Precision in the development time is critical for achieving complete removal of resist from some portions while leaving other portions substantially intact. Both insufficient development and excessive development will result in a lack of differentiation, forming a defective electronic circuit pattern on the semiconductor substrate. In addition, where the width of a conductor line(s) in the electronic circuit is critical, inadequate development results in an overly narrow line, and excessive development produces an overly wide line. Thus, precise endpoint detection (i.e., the moment at which precise development occurs) is a requirement for proper development.

Following the removal of the portions of the photo-resist material in the development process, the semiconductor wafer is subjected to further processing steps which may include doping, etching, and/or deposition of conductive materials in unprotected areas, i.e., areas devoid of photo-resist material. After one or more of these processing steps, the semiconductor wafer is subjected to a stripping step to remove the photo-resist material remaining on the semiconductor wafer.

After the removal of the photo-resist material, a subsequent processing step may include heating the semiconductor wafer in a diffusion furnace or applying a layer of material with a chemical vapor deposition system. Occasionally, a semiconductor wafer is inadvertently passed to a thermal furnace or vapor deposition system without removal or with only partial removal of the photo-resist material. The resulting damage to the processing equipment may be severe. For example, furnace diffusion tubes are irreparably damaged by vaporized hydrocarbons and carbon from the photo-resist material and, thus, the furnace diffusion tubes must be replaced. The replacement equipment and/or the downtime to repair the processing equipment is usually very costly.

Furthermore, the photo-resist carrying semiconductor wafer and one or more subsequent semiconductor wafers entering the processing equipment prior to shutdown of the equipment are usually also contaminated and must be discarded. At a late stage of manufacture, a semiconductor wafer may have a value between about $10,000 and $20,000. Thus, even an occasional loss is significant.

One method used in the industry to detect such residual photo-resist material is manual inspection with a microscope. However, manual inspection of semiconductor wafers to detect photo-resist materials has not been sufficiently effective. First, photo-resist is typically difficult to see using a conventional white light microscope, and even an experienced microscopist may inadvertently miss photo-resist on a wafer. Secondly, since manual inspection is laborious and time-consuming, it is generally not cost-effective to manually inspect more than a very small number of the semiconductor wafers (usually less than 10%). Thus, unstripped semiconductor wafers may still be missed by manual inspection.

Accordingly, an object of the present invention is to provide an improved method for rapid automated detection of resist material on semiconductor wafers in order to reduce process downtime, material wastage, maintenance/repair expenses and production costs.

SUMMARY OF THE INVENTION

The present invention is an automated method and apparatus for determining the presence or absence of a photo-resist material on the surface of a semiconductor substrate by the detection of fluorescence, reflection, or absorption of light by the photo-resist material.

Photo-resist materials are generally organic polymers, such as phenolformaldehyde, polyisoprene, poly-methyl methacrylate, poly-methyl isopropenyl ketone, poly-butene-1-sulfone, poly-trifuluoroethyl chloroacrylate, and the like. Organic substances can generally fluoresce (luminescence that is caused by the absorption of radiation at one wavelength followed by nearly immediate re-radiation at a different wavelength) or will absorb or reflect light. Fluorescence of the material at a particular wavelength, or reflection/absorption by the material of light at a given wavelength, may be detected and measured, provided the material differs from the underlying semiconductor substrate in fluorescence or reflection/absorption at a selected wavelength or wavelengths. For example, a positive photo-resist generally fluoresces red or red-orange and a negative photo-resist generally fluoresces yellow.

In a particular application of the invention, the presence of photo-resist material on a semiconductor wafer surface may be rapidly and automatically determined, recorded, and used to drive an apparatus which separates semiconductor wafers based on the presence or absence (or quantity) of the photo-resist material. Thus, semiconductor wafers which have been incompletely stripped of photo-resist material (or not stripped at all) may be automatically detected and culled from a manufacture line of fully stripped semiconductor wafers and reworked. Thus, contamination of downstream processes by unstripped semiconductor wafers is avoided.

In this invention, the semiconductor wafer is irradiated with light which may be monochromatic, multichromatic, or white. In one version, the intensity of generated fluorescence peculiar to the photo-resist material at a given wavelength is measured. In another version, the intensity is measured at a wavelength which is largely or essentially fully absorbed by the photo-resist material. In a further variation, the intensity of reflected light is measured at a particular wavelength highly reflected by the photo-resist material but absorbed by the substrate.

The intensity of fluoresced or reflected light is measured by a sensing apparatus and the result is put to a logic circuit, e.g., a computer. The result may be recorded and used for a decision making step and control of a robotic device. The robot performs the semiconductor wafer handling tasks, such as transferring the semiconductor wafers from a semiconductor wafer cassette to an inspection stage, and transferring the inspected semiconductor wafers to a destination dependent upon the test results.

A permanent record of the test results may be automatically retained and printed, and semiconductor wafers identified as being partially or totally unstripped or otherwise abnormal or defective are separated for proper disposition.

The apparatus for conducting the detection test process is generally comprised of known components which in combination produce accurate results in a very short time without laborious manual inspection. A high test rate may be achieved in a continuous or semi-continuous manufacturing process, enabling all product units to be tested. The current laborious and time-consuming testing of a few random samples by manual microscopic inspection methods is eliminated. The test results are in electronic digital form and may be incorporated into a comprehensive automated manufacturing documentation/control system.

The test apparatus may comprise a stand-alone system through which individual substrate units are passed for a separate detection/measurement step. Thus, for example, following a stripping step, semiconductor wafers may be moved sequentially through the test apparatus for confirmation of full stripping, and for culling of non-stripped semiconductor wafers.

In another version of the invention, the test apparatus may be incorporated into a processing step such as embodied in a resist stripping device for in situ determination of residual resist material on semiconductor wafers undergoing stripping. The stripping end-point may be thus determined and may be used to activate automated transfer of the stripped wafers from the resist stripper to the following process step when stripping is complete. This embodiment is particularly adaptable to plasma and wet-stripping apparatuses.

While the method and apparatus are particularly described herein as relating to the detection of photo-resist material in a lithographic process, they may also be used to detect the presence and quantity of any material on a semiconductor substrate, where the material and semiconductor substrate have differing fluorescing/absorbing properties at a given selected wavelength of radiation. The material may be an organic substance having naturally fluorescing properties under a particular spectrum of radiation, or may be a substance with little natural fluorescence, spiked with a material which fluoresces when irradiated with light of a particular wavelength.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE PREFERRED EMBODIMENTS

Figure 1:
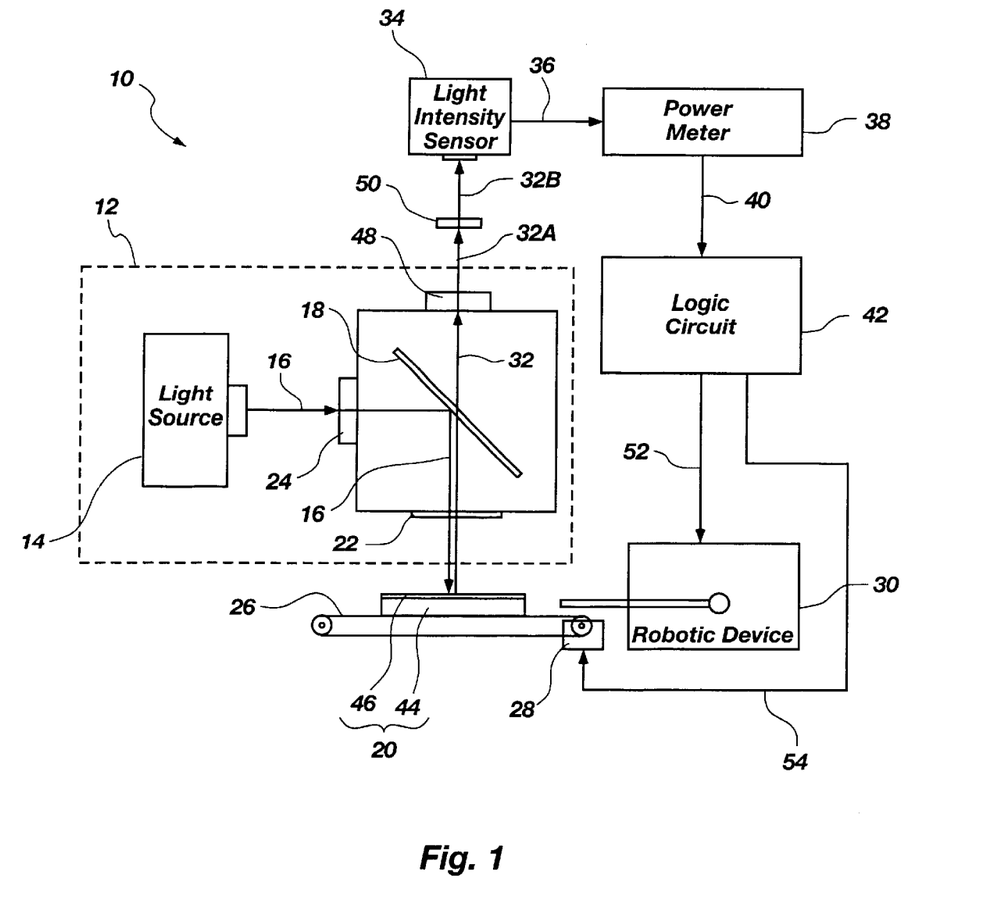
FIG. 1 is a diagrammatic view of an automated photo-resist material detection apparatus of the invention.

With reference to the drawings, and particularly to FIG. 1, one embodiment of an automated photo-resist material detection apparatus 10 of the invention is shown. The illustrated components are generally not shown to scale.

An optical portion 12 of the photo-resist material detection apparatus 10 includes a light source 14 for generating a primary light beam 16 and a dichroic or dichromatic mirror 18 for directing at least some wavelengths of the primary light beam 16 onto a sample 20, i.e., the semiconductor wafer, through a focusing lens 22. An excitation filter 24, such as a band pass filter, may be positioned in the path of primary light beam 16 for removing wavelengths from the primary light beam 16 which do not stimulate fluorescence, reflect, or absorb in the sample 20.

As well known, the dichromatic mirror 18 reflects wavelengths of less than a given value, and passes wavelengths greater than the given value.

Where fluorescence of the sample 20 is desired, light source 14 is preferably a high energy lamp such as a mercury or xenon lamp which produces high intensity fluorescence-inducing illumination.

The sample 20 is preferably mounted on a stage 26 which is movable by motive means 28 to provide the desired positioning of the sample in the primary light beam 16. A robotic device 30 loads the sample 20 onto the stage 26 and removes it after the test to another location for further processing, or alternatively, to a location for discard if the undesirable material is found on the sample 20.

A secondary light beam 32 of fluoresced light and/or reflected light emanating from the sample 20 is shown passing through the dichromatic mirror 18 to a light intensity sensor 34, such as a silicon diode sensor. The light intensity sensor 34 sends an electronic intensity signal 36 to a power meter 38, which converts the electronic intensity signal 36 into an electronic numerical value signal 40 readable by a logic circuit 42 (such as a programmable computer circuit), preferably an analog to digital conversion in the power meter 38. A small desktop computer may be used as the logic circuit 42.

The sample 20 may be a substrate 44 having a layer or coating 46 of a material which differs from the substrate in fluorescing, absorption, and/or reflection properties at some wavelengths of incident light. The sample 20 may be a semiconductor wafer comprising a slice of crystalline silicon (silicon wafer) or may include various semiconductive material or material layers, including without limitation silicon wafers, silicon-on-insulative (SOI) structure, silicon-on-sappline (SOS) structure, gallium arsenide, or germanium upon which a layer of photo-resist material has been coated, processed and subsequently stripped.

Other lenses and filters, not shown, may be used to provide the desired light beam characteristics. As shown in FIG. 1, the secondary light beam 32 of fluoresced and/or reflected light from the sample 20 is passed through a suppression filter 48 to absorb non-fluoresced light or undesired reflected light and produce a filtered light beam 32A substantially free of such undesired wavelengths. The filtered light beam 32A may be further passed through a band pass filter 50 to produce a band pass filtered light beam 32B having a narrow wavelength band of, for example, 700 nm+/−80 nm. Such a wavelength is a characteristic fluorescing emission of commonly used positive photo-resist materials, as listed above.

The optical portion 12 of the photo-resist material detection apparatus 10 may comprise a microscope adapted for measurement of the fluorescent/reflected secondary light beam 32 from the sample 20.

While the photo-resist material detection apparatus 10 may be used simply to determine the presence of a photo-resist material or other material on a substrate surface, its utility is enhanced by automation by which the samples 20 are moved to and from stage 26 by robotic device 30 as known in the art. Disposition of each sample 20 is determined by the test result therefor, and instructions 52 generated by a programmed logic circuit 42 are relayed to the robotic device 30 for proper control thereof. In a preferred embodiment, the stage 26 is moved along X-Y coordinates by instructions 54 from the logic circuit 42, enabling testing at multiple locations, preferably nine or more, on the sample 20. Because of the high rate at which the tests may be conducted, all wafers in a production line may be tested, greatly enhancing the detection of unstripped resist material.

It is also, of course, understood that the primary light beam 16 can be a sheet beam having a width approximately the width of the sample 20. The sample 20 can be passed through the sheet beam which will result in the inspection of the entire surface of the sample 20.

In one embodiment of the photo-resist material detection apparatus 10, the power meter 38 converts the electronic intensity signal 36 into a simple digital "0" or "1" value, depending upon whether the electronic intensity signal 36 is less than or more than a selected cutoff value. This is useful when the decision is simply one of acceptance or rejection.

In other embodiments of the photo-resist material detection apparatus 10, the power meter 38 may produce an electronic numerical value signal 40 representative of (in proportion to) the measured light intensity.

The detection surface test area of the sample 20 which provides the fluoresced or reflected secondary light beam 32 for a test may vary, depending upon the desired resolution. Thus, for detecting the presence of photo-resist material on a narrow slot location of a wafer, the diameter of the measurement circle may be very small, e.g., less than a fraction of a mil. The measurement of light intensity from such small areas may require prior light amplification. However, for some applications, the measurement circle may be much larger, and light amplification may not even be required.

Figure 2:
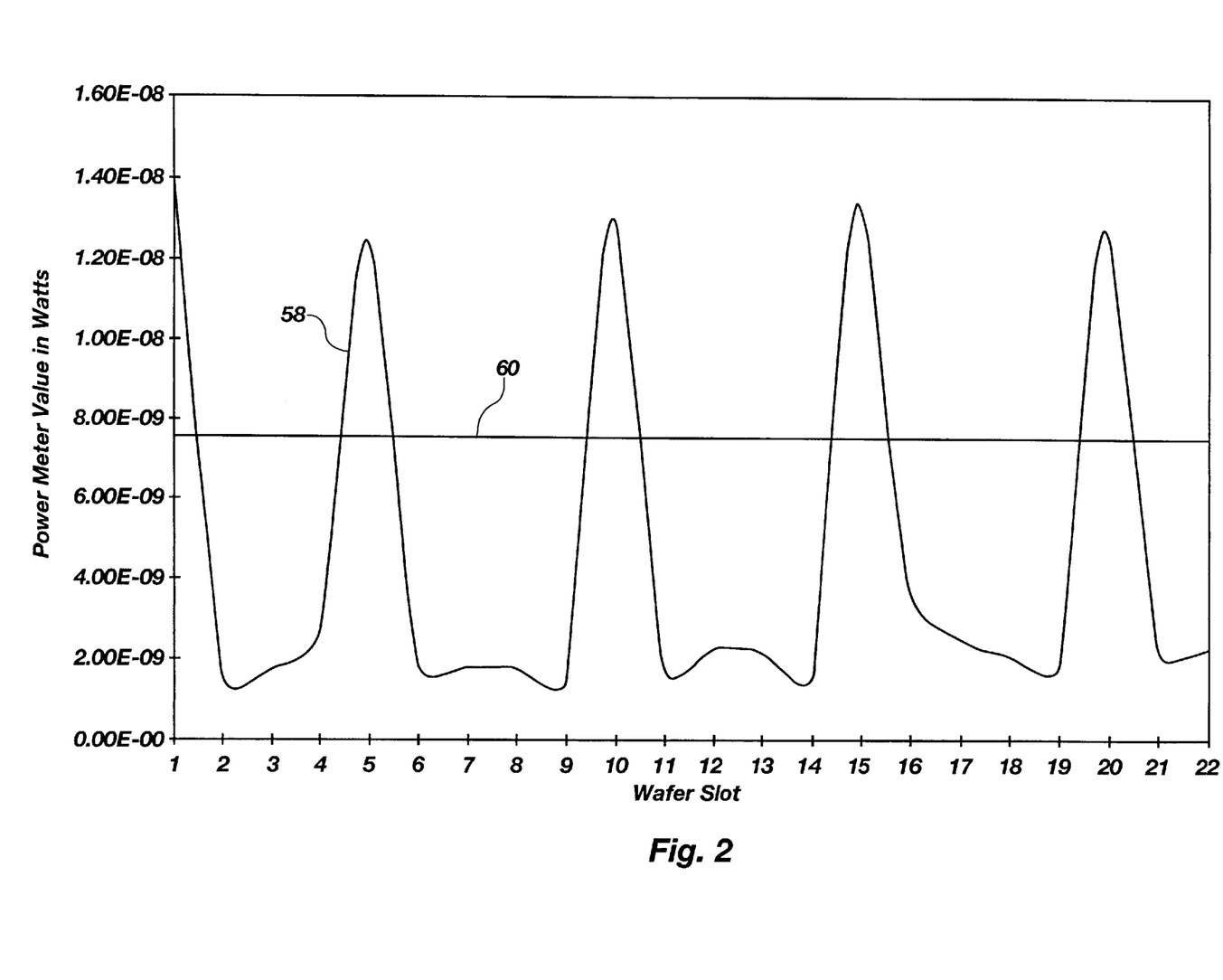
FIG. 2 is a graphical representation of exemplary results of detection tests conducted on a series of semiconductor wafers.

FIG. 2 shows the fluoresced light intensity output from the apparatus of FIG. 1, where tests were conducted on a series of twenty-two substrates 44 in the form of semiconductor wafers. Stripped slots were formed on all but five of the semiconductor wafers (numbers 1, 5, 10, 15 and 20) which remained unstripped. Three tests were conducted on each semiconductor wafer, the results averaged by computer and printed as a continuous line 58. Light intensities are shown in watts, as determined by the power meter 38. The unstripped semiconductor wafers produced light intensity values of about $(1.2 \text{ to } 1.4) \times 10^{-0.08}$ watts, while intensity values were about $(1.0 \text{ to } 2.0) \times 10^{-0.09}$ watts for the stripped semiconductor wafers. As shown, an intermediate cutoff value 60 of light intensity may be selected as the basis for acceptance/rejection of each semiconductor wafer 56 by the robotic device 30.

Figure 3:
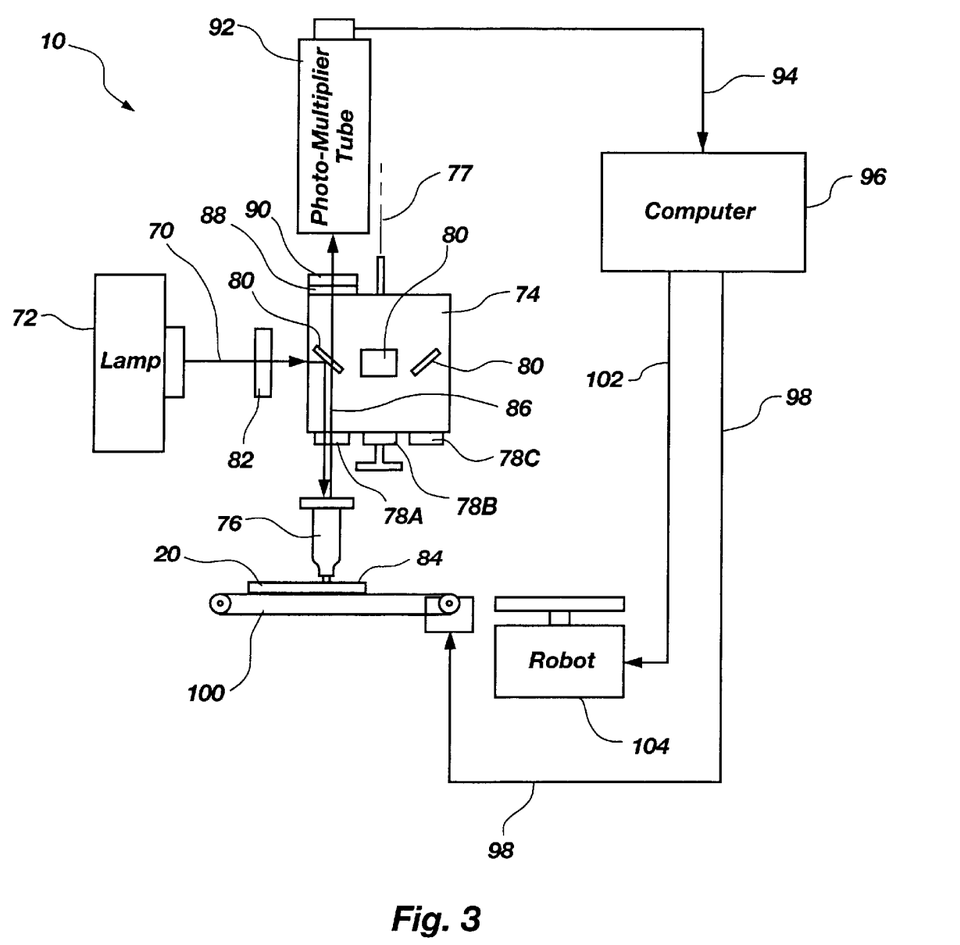
FIG. 3 is a diagrammatic view of a further embodiment of the automated photo-resist material detection apparatus of the invention.

Another version of the photo-resist material detection apparatus 10 of the invention is shown in FIG. 3. A primary beam 70 of high intensity radiation is generated by a lamp 72 and directed into a filter cube 74 to be reflected onto the sample 20 through a focusing lens 76. As available commercially, filter cubes 74 comprise a plurality of optical light paths as exemplified by 78A, 78B, and 78C, each with a dichroic mirror 80 for directing primary beam 70 optionally through optical filters 82 of differing characteristics, through the focusing lens 76 onto the surface 84 of the sample 20. The filter cube 74 is rotatable about a vertical axis 77 for selectively aligning a desired optical light path 78A–C with the high intensity lamp 72 and focusing lens 76. The dichroic mirrors 80 in the selectable optical light paths 78A–C may have different reflectance properties. The fluoresced and reflected light (output light) 86 from the sample 20 passes back through the focusing lens 76 and selected dichroic mirror 80 of the filter cube 74, and through optional optical filter 88 to an output lens 90 normally used for observation.

As illustrated in FIG. 3, the output light 86 from the output lens 90 of the filter cube 74 is directed into a photo-multiplier tube (PMT) 92 which sends an electronic signal 94 to a computer 96 for recording, analysis and decision making. Signals 98 generated by computer 96, programmed with appropriate software, control movement of the stage 100. Signals 102 control robot 104 for sample movement onto the stage 100 and for disposition of the tested sample 20 from the stage.

The use of the filter cube 74 enables a rapid trial of various wavelengths of fluoresced/reflected light to determine the most advantageous output wavelength for production testing.

Figure 4:
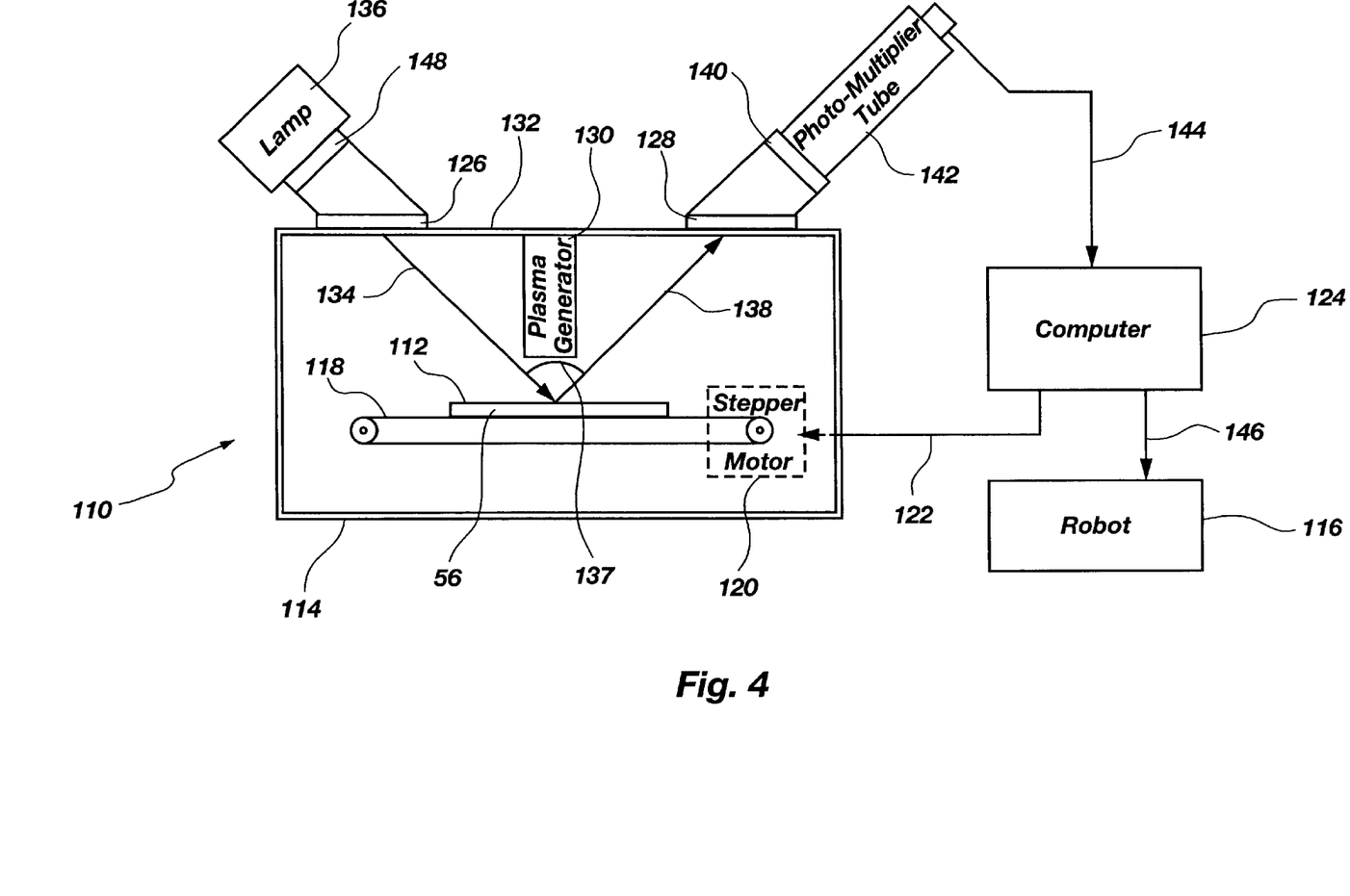
FIG. 4 is a diagrammatic view of an additional embodiment of the automated photo-resist material detection apparatus of the invention.

As shown in FIG. 4, the photo-resist material detection apparatus 10 may be incorporated into a stripping tool 110 for in situ automated determination of the progress in stripping of material layer 46 from the surface 112 of a semiconductor wafer 56. Elements common between FIGS. 1–3 and FIG. 4 retain the same numeric designation. The stripping process may comprise wet- or dry-stripping performed in a stripping chamber 114. The stripping chamber 114 is illustrated herein with a plasma generator 130. The stripping chamber 114 has one or two entryways, not shown, for the introduction and removal of the semiconductor wafers 56 by a robot 116. The semiconductor wafer 56 is shown on a movable stage 118 within the stripping chamber 114. The movable stage 118 may be movable by one or more stepper motors 120 or other motive means controlled by electronic signals 122 from a computer 124.

Two optical ports 126, 128 are positioned in a wall 132 of the stripping chamber 114. A primary high energy beam 134 of light from lamp 136 passes through a first optical port 126, strikes the surface 112 of the semiconductor wafer 56 and is reflected as reflected beam 138 at an angle through the second optical port 128. Fluoresced and/or reflected light produced by existing material layer 46 on surface 112 in response to the primary high energy beam 134 is also present in reflected beam 138. The reflected beam 138 is passed through an optical band pass filter 140 and into a photomultiplier tube 142 for generation of an electronic signal 144 indicative of the light intensity at the filtered light wavelength. The electronic signal 144 is received by a software program in the computer 124 and processed to provide instructions 146 to the robot 116 for removal of the wafer 56 from the stripping chamber 114. Electronic signals 122 are also sent by computer 124 for controlling motion of the movable stage 118.

The primary high energy beam 134 is shown in FIG. 4 as striking the wafer 56 at an angle of about 45 degrees. The angle 137 between primary high energy beam 134 and reflected beam 138 is preferably between 0 and 90 degrees. However, by using a dichromatic mirror as in FIGS. 1 and 3, primary high energy beam 134 and reflected beam 138 may both pass through the same optical port 126 or 128, and angle 137 is 0 degrees.

The high energy lamp 136 is typically a mercury or xenon lamp, and the output may be filtered by a band pass filter 148 to provide the desired wavelengths for producing fluorescence, reflectance, and/or absorption in the particular resist material.

As indicated, the method depends upon a difference in fluorescence or light absorption/reflectance between the material to be detected, e.g., the photo-resist and the underlying substrate. A wavelength of incident illumination is typically chosen which maximizes the difference in fluorescence, absorption, or reflectance. It is preferred to use fluorescence as the measured output, but light absorbance may be used when the material to be detected strongly absorbs a particular wavelength of radiation while the substrate strongly reflects the same.

It should be understood that references herein to light of a particular "wavelength" encompass wavelength bands that are "about" a particular wavelength. In other words, the term "a particular wavelength" may include wavelengths both slightly longer and shorter than the "particular wavelength".

The advantages of this method over prior resist inspection methods are substantial.

First, the test is rapid and automated, enabling all wafers to be tested. The inadvertent passage of unstripped wafers to downstream process equipment, with concomitant costly contamination and destruction of the equipment, may be virtually eliminated.

Second, laborious and time-consuming visual inspections for resist are eliminated. Such tests are less than adequate, in any case.

Third, the detection method is adaptable to any type of resist or other material which may be applied to a substrate surface. This is because the process may be based on the quantitative differences between the material and the substrate in fluoresced light, reflected light, or absorbed light. Particular wavelengths are chosen to accentuate these differences.

Fourth, the apparatus for conducting the automated resist detection tests comprises an assembly of readily available equipment items.

Fifth, the software program for controlling the robot and movable stage may be very simple and easy to construct.

Sixth, the process and equipment may be readily incorporated in a batch, continuous or semi-continuous manufacturing process for accurate in situ determination of the end-point of resist stripping. Such use enhances the accuracy of end-point determination.

Seventh, the automated test method and control thereof may be incorporated in a comprehensive manufacturing documentation and control system.

Eighth, the method may be used to determine the presence of a material in a very small area, or alternatively in a relatively large area, by using an appropriate optical lens.

Having thus described in detail preferred embodiments of the present invention, it is to be understood that the invention defined by the appended claims is not to be limited by particular details set forth in the above description, as many apparent variations thereof are possible without departing from the spirit or scope thereof.

What is claimed is:

1. An apparatus for determining the presence of a material on a substrate, comprising:

a stage for positioning a substrate;

a first optical apparatus for forming a beam of light and directing the beam of light to a location on a surface of the substrate, the first optical apparatus including a filter cube comprising a plurality of dichroic mirrors and a plurality of selectable light paths;

a second optical apparatus for collecting light emanating from the location on the surface of the substrate and directing the light through a band pass filter; and a light intensity sensing apparatus for measuring the intensity of the light emanating from the location on the surface of the substrate.

2. The apparatus of claim 1, further comprising a means for generating an electronic signal representative of the intensity of the light emanating from the location on the surface of the substrate.

3. The apparatus of claim 1, further comprising a logic circuit for processing an electronic signal representative of the intensity of the light emanating from the location on the surface of the substrate.

4. The apparatus of claim 1, further comprising an automated substrate handling apparatus for moving the substrate to and from the stage.

5. The apparatus of claim 1, further comprising an automated substrate handling apparatus and a plurality of off-stage sites, the automated substrate handling apparatus capable of selectively moving the substrate to any one of the plurality of off-stage sites.

6. The apparatus of claim 1, wherein the stage is configured to position the substrate at a plurality of measurement sites.

7. The apparatus of claim 1, wherein the stage is configured to position the substrate at a plurality of measurement sites and the apparatus further comprises an automated substrate handling apparatus and a computer capable of receiving an electronic signal representative of the intensity of the light emanating from the location on the surface of the substrate, instructing the stage to position the substrate at one of said plurality of measurement sites, and instructing the automated substrate handling apparatus to move the substrate to and from the stage.

8. The apparatus of claim 1, wherein the first optical apparatus comprises a band pass filter capable of restricting the beam of light to a predetermined wavelength band.

9. The apparatus of claim 1, wherein the first optical apparatus comprises an excitation filter capable of restricting the beam of light to a predetermined wavelength that induces fluorescence in the material.

10. The apparatus of claim 1, wherein the first optical apparatus comprises a band pass filter capable of restricting the beam of light to wavelengths which are substantially absorbed by the material and substantially reflected by the substrate.

11. The apparatus of claim 1, wherein the first optical apparatus comprises a band pass filter capable of restricting the beam of light to wavelengths which are substantially reflected by the material and substantially absorbed by said substrate.

12. The apparatus of claim 1, further comprising a high energy light source.

13. The apparatus of claim 1, further comprising a high energy light source selected from a group consisting of a xenon lamp and a mercury lamp.

14. The apparatus of claim 1, wherein the light intensity sensing apparatus comprises a silicon diode sensor capable of producing a light intensity measurement.

15. The apparatus of claim 1, wherein said light intensity sensing apparatus includes a power meter capable of converting a light intensity measurement into a digital form.

16. The apparatus of claim 1, wherein said light intensity sensing apparatus comprises a photo-multiplier tube.

17. An apparatus for determining the presence of a material on a substrate, comprising:

a stage for positioning a substrate;

a first optical apparatus for forming a beam of light and directing the beam of light to a location on a surface of the substrate, the first optical apparatus including a filter cube comprising a plurality of dichroic mirrors and a plurality of selectable light paths;

a second optical apparatus for collecting light emanating from the location on the surface of the substrate and directing the light through a band pass filter;

a light intensity sensing apparatus for measuring the intensity of the light emanating from the location on the surface of the substrate; and a resist-stripping chamber enclosing at least said stage.

* * * * *

UNITED STATES PATENT AND TRADEMARK OFFICE
CERTIFICATE OF CORRECTION

PATENT NO. : 6,369,887 B2
DATED : April 9, 2002
INVENTOR(S) : Mark Eyolfson et al.

It is certified that error appears in the above-identified patent and that said Letters Patent is hereby corrected as shown below:

Column 3,
Line 26, change "put" to -- input --.
Line 39, after "components" insert a comma -- , --.

Column 4,
Line 49, after "As" insert -- is --.
Lines 53 and 54, after "lamp" insert a comma -- , --.
Line 56, after "26" insert a comma -- , --.
Line 58, after "sample" insert -- 20 --.

Column 5,
Line 13, after "limitation" insert a comma -- , --.
Line 15, change "sappline" to -- sapphire -- and after "germanium" insert a comma -- , --.
Line 24, after "wafer" delete "56".
Line 53, after "beam" insert a comma -- , --.

Column 6,
Line 48, after "92" insert a comma -- , --.

Column 7,
Line 44, after "chosen" insert a comma -- , --.

Signed and Sealed this

Twenty-fifth Day of April, 2006

JON W. DUDAS
*Director of the United States Patent and Trademark Office*